US012685579B2

(12) United States Patent
Krüger et al.

(10) Patent No.: US 12,685,579 B2
(45) Date of Patent: Jul. 21, 2026

(54) THERMAL MANAGEMENT OF AN ELECTROSURGICAL GENERATOR

(71) Applicant: OLYMPUS WINTER & IBE GMBH, Hamburg (DE)

(72) Inventors: Jens Krüger, Zeuthen (DE); Stefan Schiddel, Stahnsdorf (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 405 days.

(21) Appl. No.: 18/209,200

(22) Filed: Jun. 13, 2023

(65) Prior Publication Data

US 2023/0404645 A1 Dec. 21, 2023

Related U.S. Application Data

(60) Provisional application No. 63/352,701, filed on Jun. 16, 2022.

(51) Int. Cl.
*A61B 18/12* (2006.01)
*A61B 17/00* (2006.01)
*A61B 18/00* (2006.01)

(52) U.S. Cl.
CPC .............................. *A61B 18/1206* (2013.01); *A61B 2017/00199* (2013.01); *A61B 2017/00973* (2013.01); *A61B 2018/00928* (2013.01)

(58) Field of Classification Search
CPC ...... A61B 18/1206; A61B 2017/00199; A61B 2017/00973; A61B 2018/00928
USPC ......................................................... 606/34
See application file for complete search history.

(56) References Cited

U.S. PATENT DOCUMENTS 8,452,463 B2 5/2013 Cox et al.

FOREIGN PATENT DOCUMENTS

EP 3804647 A1 4/2021
WO WO-2020245959 A1 * 12/2020 ..... A61B 17/320068

OTHER PUBLICATIONS

Feb. 17, 2023 Office Action issued in German Patent Application No. 10 2022 115 204.9.

* cited by examiner

*Primary Examiner* — Beverly M Flanagan
(74) *Attorney, Agent, or Firm* — Oliff PLC

(57) ABSTRACT

An electrosurgical generator for operating an electrosurgical instrument is characterized by a control device which is adapted to control a cooling device at least with a first control curve and a second control curve, wherein the first control curve is used to control the rotational speed of the cooling device depending on the monitored temperature during a first operating mode of the electrosurgical generator and the second curve is used to control the rotational speed of the cooling device depending on the monitored temperature during a second operating mode of the electrosurgical instrument, wherein the first control curve and the second control curve are different from each other. A method for operating an electrosurgical generator for operating an electrosurgical instrument and to an electrosurgical generator system includes an electrosurgical generator and an electrosurgical instrument.

20 Claims, 4 Drawing Sheets

Fig. 1

THERMAL MANAGEMENT OF AN ELECTROSURGICAL GENERATOR

TECHNICAL FIELD

The present invention relates to an electrosurgical generator for operating an electrosurgical instrument. The present invention also relates to a method for operating an electrosurgical generator for operating an electrosurgical instrument. The present invention also relates to an electrosurgical generator system comprising an electrosurgical generator and an electrosurgical instrument.

BACKGROUND

Known electrosurgical generator use for example linear temperature control for controlling housing cooling devices of the generator, such as fans or heat pumps or evaporative cooler. One or more temperature sensors arranged near or on critical device hardware are monitored, such as coils, switching FETs or the like,. Such a temperature management and control structure is known as active cooling. Active cooling in general is a heat-reducing mechanism that is typically implemented in electronic devices to ensure proper heat transfer and circulation from within.

It is known to control for example a fan speed depending on the temperature. If the measured temperature increases the fan speed is increased using a linear function or linear factor. The linear function or linear factor is implemented in the control mechanism of the generator and in the control device controlling the cooling device. The linear factor can also be understood as slope or gradient of the linear function that defines how fast the fan speed increases depending on the temperature. Furthermore, it is known to switch on the fan, when a minimum temperature is reached. For that purpose, it is known that a offset constant controls the minimum temperature, when the fan is switched on, thus starts spinning. The offset constant can be understood as a threshold value for the temperature. When the offset constant is reached, the fan starts spinning. Such an offset constant is used in order to reduce the energy consumption and the noise of the generator, when the measured temperature of the critical device hardware is low enough a no cooling is needed. So both parameters "offset" and "factor" control the fan speed dependent from the temperature sensor (s).

Electrosurgical generators include different operating states like an activation state, a standby state or a deactivation state. In the activation state the electrosurgical generator is active and adapted to supply the electrosurgical instrument with electrical power. The activation state can also be understood as an operating mode or an active mode. The electrosurgical generator also includes a standby state in which parts of the generator are switched into a standby mode in order to save energy. Furthermore, a deactivation state is known in which parts of the generator are deactivated In known electrosurgical generators the temperature control algorithm works independently from the states of the generator, which causes problems.

Especially in semiconductors the temperatures can increase very quickly during operation. Dependent from measurement and reaction speed (sampling rate and control algorithm frequency) the temperature might increase very fast, when an electrosurgical instrument is activated and supplied with high frequency (HF) energy. The fan itself is however is limited in reaction speed, e.g. in transition from standing fan blades to full rotation.

In result, excessive heat may not be removed quickly enough from the electrical generator and the critical hardware components. This may result in temporary hotspots in the device electronic, which can lead to early system or component failure.

SUMMARY

Therefore, it is an object of the present invention to provide a heat-reducing mechanism for an electrosurgical generator that ensures a proper heat transfer and circulation from within the generator. In particular, it is an object of the present invention to provide a solution, which increases the reliability of the electrosurgical generator and prevents overheating of critical hardware components of the electrosurgical generator.

According to a first aspect of the invention an electrosurgical generator for operating an electrosurgical instrument according to claim 1 is suggested.

The electrosurgical generator is thus adapted to supply the electrosurgical instrument with power and to operate the instrument. The generator is configured to supply the instrument with a current and/or a voltage electrically. The generator is connected for that purpose for example with an electrical supply grid and includes a power converter for power supply of the instrument. The power converter can also be referred to as switching device. Power converters are generally known. The generated current provided to the instrument can be higher, lower or inverted depending on the design of the converter and the requirements of the electrical load, respectively the electrosurgical instrument. The generator may also include a rectifier to convert the received AC current from the electrical supply grid. The generator includes instrument terminals or ports for connecting the electrosurgical instrument with the generator for power supply and/or data or signal exchange.

The electrosurgical generator for operating the electrosurgical instrument comprises a housing. The housing is an exterior case or enclosure used to protect the interior components of the electrosurgical generator. The housing prevents the interior parts from being fouled by outside debris.

The electrosurgical generator also includes an active controllable cooling device for removing heat energy generated within the housing, wherein a rotational speed of the cooling device is temperature-controlled. The cooling device is for example a fan or heat pump or evaporative cooler. Preferably, the cooling device is a fan. The cooling device includes a controllable drive whose rotational speed is controllable. The unit for the rotational speed is revolutions per minute (RPM). It is thus suggested that the cooling device changes its rotational speed depending on a measured temperature of parts or components of the generator.

For that purpose, the electrosurgical generator includes at least one temperature sensor for monitoring a temperature of a hardware component of the electrosurgical generator. The hardware component is for example a critical hardware component such as coil, wires, switching transistor or the like. A transistor is a semiconductor device used to amplify or switch electrical signals and power, wherein known transistors are for example FETs, which is the abbreviation of field effect transistors. Suitable temperature sensors are known, for example temperature sensors that change their resistance depending on the temperature, such as PT, NTC or PCT sensors or the like. One or more sensors can be used in order to measure the temperature at different hardware components.

The electrosurgical generator also includes a control device for controlling the cooling device, in particular depending on the measured temperature and depending on a present operating mode of the electrosurgical generator. The control device is for example a microcontroller or a central processing unit of the generator. The control device is adapted to control the rotational speed of the cooling device. The control device is interconnected with the cooling device and the temperature sensor(s).

Thus, a heat-reducing mechanism for an electrosurgical generator is suggested to ensure a proper heat transfer and circulation from within the generator. The control device interconnected with the cooling device and the temperature sensors forms an active cooling.

According to the invention, the control device is adapted to control the cooling device at least with a first control curve and a second control curve. It is thus suggested to implement at least a first control curve and a second control curve in the control device of the electrosurgical generator, which are different from one another. In case a fan is used, the control curve is a fan control curve for instance. The control device may include for that purpose a data store or a memory unit in order to store the control curves. The data store or memory unit is preferably non-volatile. The wording "at least" expresses that a plurality of control curves can be used, each control curve being dedicated or assigned to one operating mode, for example three or more control curves for different purposes.

The first control curve is used to control the rotational speed of the cooling device depending on the monitored temperature during a first operating mode of the electrosurgical generator and the second curve is used to control the rotational speed of the cooling device depending on the monitored temperature during a second operating mode of the electrosurgical instrument, wherein the first control curve and the second control curve are different from each other. The term mode can also be understood as state. It is thus suggested to use different control curves during the operating states or modes of the generator. When the first operating mode of the generator is active, the first control curve is used to control the rotational speed of the cooling device depending on the measured temperature. When the second operating mode of the generator is active, the second control curve is used to control the rotational speed of the cooling device depending on the measured temperature. The same principle applies for more than the two operating modes.

The first and second control curve can be implemented as look-up tables or software functions or the like in the electrosurgical generator.

It was discovered that the cooling requirements and heat generation of the generator is different during the different operating states of generator. For example in the standby state a different amount of heat energy is generated in the generator compared to the operating state, when for example HF energy is generated and provided to the electrosurgical instrument. It was discovered that a classical control with only one control curve causes problems, in particular in the transition between the operating modes, thus, when the modes of the generator change.

Especially in semiconductor switches used to generate HF energy, the temperatures can increase very quickly during operation. Dependent from measurement and reaction speed of the cooling device the temperature of the switches may increase very fast, when an electrosurgical instrument is activated and supplied with high frequency (HF) energy. Both the temperature measurement with the temperature sensors and the rotational speed adjustment of the cooling device have a time delay, which can be critical. A fan is for example limited in reaction speed, e.g. in transition from standing fan blades to full rotation. Due to the said delay, it may happen that the transistors already have reached a damaging temperature before the cooling effect of the cooling device is sufficiently strong. In result, excessive heat may not be removed quickly enough from the electrical generator. This may result in temporary hotspots in the device electronic, which can lead to early system or component failure. In order to react precautionary, it is thus suggested to use different control curves in order to provide a situation suitable control curve for each operating state of the generator. Thereby, the effect is exploited that the switching between operating states of the generator requires a short period of time and this period of time can be used in order to control the cooling device in a precautionary manner, for example by driving the rotational speed to a minimum rotational speed with a second control curve.

Therefore, by means of operating mode depending control curves, an heat-reducing mechanism for an electrosurgical generator is provided that ensures proper heat transfer and circulation from within the generator, which increases the reliability of the electrosurgical generator and prevents overheating of critical hardware components of the electrosurgical generator.

Preferably, the first operating mode is a standby mode in which no electrosurgical instrument is connected to the electrosurgical generator or a connected electrosurgical instrument is not supplied with electrical power from the electrosurgical generator. The electrosurgical generator thus includes a standby mode or standby state in which parts of the generator are switched into standby in order to save energy. In the standby mode no electrical HF energy is provided to the electrosurgical instrument. The standby mode can be understood as a sleep mode or energy saving mode or idle mode. This mode may be activated for example by means of trigger signal or when a predefined timer has expired, which is stored in the control device.

Preferably, the second operating mode is an activation mode in which an electrosurgical instrument is connected to the electrosurgical generator and is supplied with electrical power from the electrosurgical generator. The activation state can also be understood as operating mode or active mode or HF mode. In the activation mode the electrosurgical generator is active and adapted to supply the electrosurgical instrument with power, in particular with HF energy. It is understood that for this purpose an electrosurgical instrument is connected to the generator at an instrument terminal.

Preferably, the electrosurgical generator includes a manual trigger device, wherein the manual trigger device is adapted to trigger a switching between the first operating mode and the second operating mode of the generator. The manual trigger device may be connected to the generator at a terminal or port for the trigger device. It is thus suggested that the changeover or switching between the operating modes and thus between the control curves is manually triggered by means of a manual switch.

Preferably, the manual trigger device is a hand switch and/or a foot switch connected to the electrosurgical generator. The hand switch may be integrally formed in or at an electrosurgical instrument. The hand switch may also be an external hand switch connected with the generator. The foot switch is preferably an external foot switch connected at a foot switch terminal of the generator. Thus, it is suggested to activate the different operating modes of the generator with manual switches arranged outside the generator.

Preferably, the manual trigger device is a switching mean and/or input mean, which is integrated into the housing of the electrosurgical generator. The switching mean or input mean is for example a button or touch display arranged at the electrosurgical generator. Thus, it is suggested to activate the different operating modes of the generator with switches arranged at the generator.

Preferably, the first control curve increases the rotational speed of the cooling device depending on the monitored temperature, in case the monitored temperature of the hardware component exceeds a first minimum temperature value, and wherein the rotational speed of the cooling device is set to zero, when the monitored temperature is below the first minimum temperature value. It thus suggested that the cooling device is turned on, when the measured temperature at the monitored hardware components reaches or oversteps the first minimum temperature value. The first minimum temperature value can also be understood as a first temperature threshold value. Below this first threshold value the cooling device is turned off. Further preferred the first control curve increases the rotational speed of the cooling device with a rising function, when the measured temperature increases and when the temperature is above the first minimum temperature value. For that purpose, a rising function is implemented in the control device, such as a linear rising function with a linear factor or a quadratic rising function or exponentially rising function or the like. The rising function is preferably a manual adjustable function, which can be displayed at a display device of the generator and can be adjusted by user inputs. This way, an individual adjustable rising function is implemented in the generator.

Preferably, the second control curve increases the rotational speed of the cooling device depending on the monitored temperature, in case the monitored temperature of the hardware component exceeds a second minimum temperature value, and wherein the rotational speed of the cooling device is set to minimum rotational speed value when the monitored temperature is below the second minimum temperature value. It thus suggested that the cooling device is always turned on and rotates with a minimum rotational speed in the second operating mode, when the monitored temperature is below the second minimum temperature value. The second minimum temperature value can also be understood as a second temperature threshold value. The second minimum temperature value can be different from the first minimum temperature value. Below the second threshold value the cooling device is operated with a minimum rotational speed which is greater than zero. Further preferred the second control curve increases the rotational speed of the cooling device with a rising function, when the measured temperature increases and when the temperature is above the second minimum temperature value. For that purpose, a rising function is implemented in the control device, such as a linear rising function with a linear factor or a quadratic rising function or exponentially rising function or the like. The rising function is preferably a manual adjustable function, which can be displayed at a display device of the generator and can be adjusted by user inputs. This way, an individual adjustable rising function is implemented in the generator.

Preferably, the control device is adapted to control the cooling device additionally with a third control curve, wherein the third curve is used to control the rotational speed of the cooling device depending on the monitored temperature and wherein the third control curve is activated, when the second operating mode is deactivated. It is thus suggested to activate the third control curve, when the second operation mode is deactivated. The third control curve is used to ramp down the temperature of the hardware component of the electrosurgical generator directly after the second operating mode, which is in particular the activation mode as described above. The third curve can therefore be used in a cooling phase of the hardware components, when the instrument is not supplied with HF energy anymore. Further preferred the third control curve is different from the first and second control curve. Further preferred, the rotational speed of the cooling device is set to a cool down rotational speed value by means of the third control curve. The cool down rotational speed value is a rotational speed value, which is greater than zero and can be set to an individual value. Preferably, the third control curve is activated until a predefined time duration is reached or until a predefined temperature of the hardware components is reached. The third control curve can thus be understood as a control curve that is used to ramp down the temperature of the hardware components in a fast manner, after the electrosurgical instrument is supplied with power. It can also be understood as a temporary control curve.

According to a further aspect of the invention a method for operating an electrosurgical generator for operating an electrosurgical instrument is suggested, wherein the method comprises the steps of: Providing an active cooling device for removing heat energy generated within a housing of the electrosurgical generator; Monitoring a temperature of a hardware component of the electrosurgical generator by means of at least one temperature sensor; and Controlling the cooling device by means a control device, wherein the controlling includes controlling the cooling device with at least a first control curve and a second control curve, wherein the first control curve is used to control the rotational speed of the cooling device depending on the monitored temperature during a first operating mode of the electrosurgical generator and the second curve is used to control the rotational speed of the cooling device depending on the monitored temperature during a second operating mode of the electrosurgical instrument.

Regarding to the electrosurgical generator, the electrosurgical instrument, housing, the active cooling device, the hardware components, the temperature sensor, the cooling device and the first and second control curves, it is referred to the advantages, explanations and definitions as described above, which apply analog to the method described above and below.

The first step of the method is thus to provide an active cooling device to remove generated heat energy from the interior of the housing of the electrosurgical generator. The cooling device is for example a controllable fan. A further step is to monitor the temperature of hardware components of the generator. This step can be understood as a measuring step. The temperature monitoring is continuously performed. The measured temperature is used to control the cooling device by means of a control device. Thus, a further step is to control the cooling device with a control device, which is for example a microcontroller or a processing unit. The controlling thereby includes a control with a first and second control curve, which can be understood in case of a fan as a fan control curve. Two different curves are used for two different operating modes. Thus, it is suggested to assign each control curve to a specific operating mode. When the first operating mode of the generator is active, the first control curve is used to control the rotational speed of the cooling device depending on the measured temperature. When the second operating mode of the generator is active, the second control curve is used to control the rotational speed of the cooling device depending on the measured temperature. The same principle applies for more than the two operating modes.

Preferably, the first operating mode is a standby mode in which no electrosurgical instrument is connected to the electrosurgical generator or a connected electrosurgical instrument is not supplied with electrical power from the electrosurgical generator, in particular as described above.

Preferably, the second operating mode is an activation mode in which an electrosurgical instrument is connected to the electrosurgical generator and is supplied with electrical power from the electrosurgical generator, in particular as described above.

Preferably, the method includes the further step of: Triggering a switching between the first operating mode and the second operating mode of the generator by means of a manual trigger device, in particular as described above. The trigger device is preferably a hand switch, a foot switch, a switching mean and/or an input mean or the like, as described above. Thus, a manual switching step of the operating modes is suggested.

Preferably, the controlling step includes the further step of increasing the rotational speed of the cooling device by means of the first control curve depending on the monitored temperature, in case the monitored temperature of the hardware component exceeds a first minimum temperature value, and wherein the rotational speed of the cooling device is set to zero, when the monitored temperature is below the first minimum temperature value.

Further preferred the controlling step includes the step of increasing the rotational speed of the cooling device with the first control curve by means of a rising function, when the measured temperature increases, in particular increasing the rotational speed by means of a linear rising function, a quadratic rising function or an exponential rising function or the like.

Further preferred the controlling step includes the step of providing a manual adjustable function as rising function, which can be displayed at a display device of the generator and can be adjusted by user inputs.

Preferably, the controlling step includes the further step increasing the rotational speed of the cooling device by means of the second control curve depending on the monitored temperature, in case the monitored temperature of the hardware component exceeds a second minimum temperature value, and wherein the rotational speed of the cooling device is set to minimum rotational speed value, when the monitored temperature is below the second minimum temperature value.

Further preferred the controlling step includes the step of increasing the rotational speed of the cooling device with the second control curve by means of a rising function, when the measured temperature increases, in particular increasing the rotational speed by means of a linear rising function, a quadratic rising function or an exponential rising function or the like.

Further preferred the controlling step includes the step of providing a manual adjustable function as rising function, which can be displayed at a display device of the generator and can be adjusted by user inputs.

According to a further aspect of the invention an electrosurgical generator system is suggested that comprises an electrosurgical generator and an electrosurgical instrument, wherein the electrosurgical generator comprises at least one instrument terminal for connecting and electrically supplying the electrosurgical instrument, wherein during operating the electrosurgical generator system the electrosurgical instrument is connected to the instrument terminal, wherein the electrosurgical generator is configured according to at least on of the preceding or succeeding embodiments and/or is adapted to perform the method according to one of the preceding or succeeding embodiments.

As to the advantages, preferred embodiments and details of this further aspect and its preferred embodiments, reference is made to the corresponding advantages, preferred embodiments and details described above.

BRIEF DESCRIPTION OF THE DRAWINGS

Preferred embodiments shall now be described with reference to the attached figures, in which.

In the figures, elements with the same or comparable functions are indicated with the same reference numerals.

DETAILED DESCRIPTION

Figure 1:
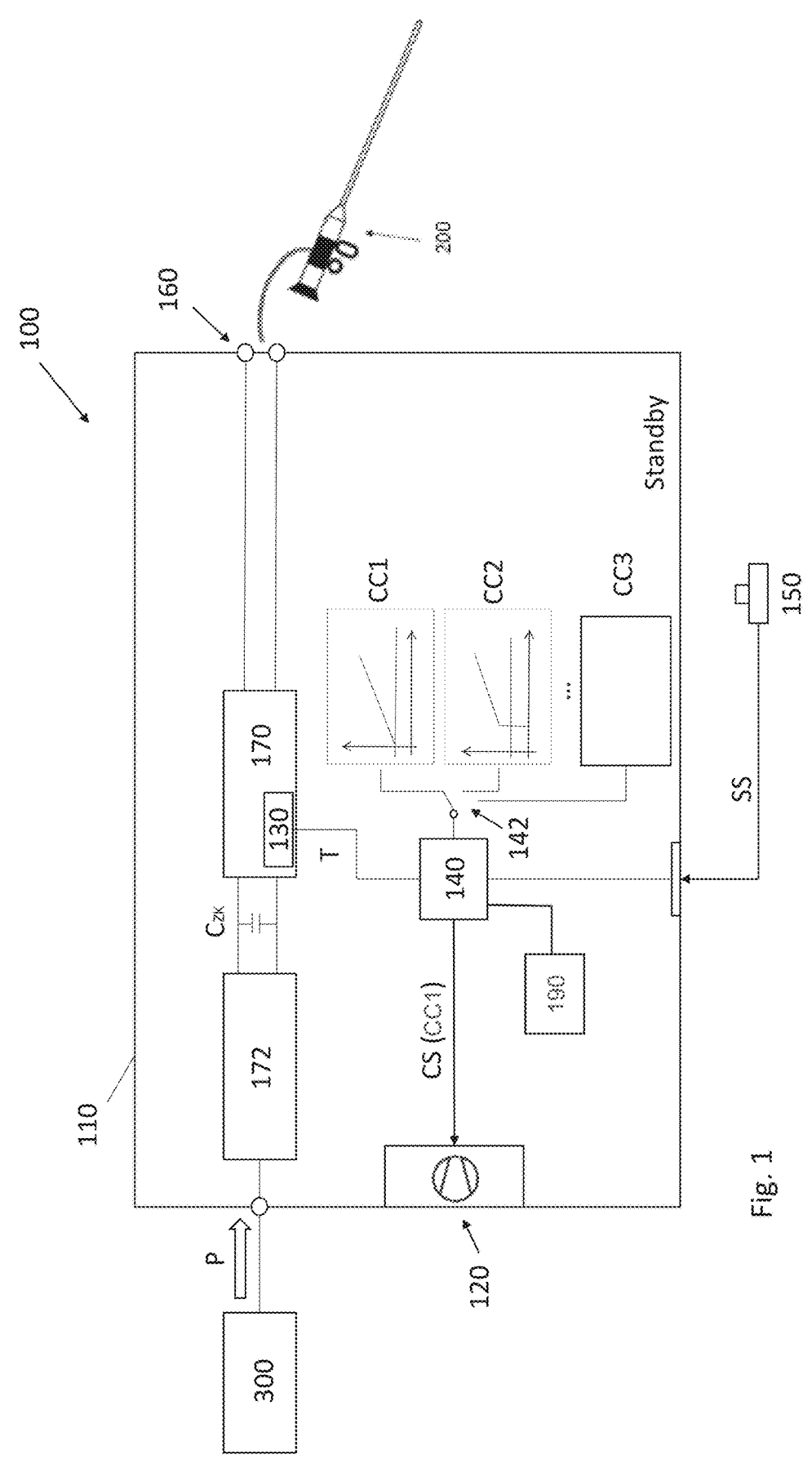
FIG. 1 shows an electrosurgical generator in an embodiment according to the invention with a control device that is adapted to control a cooling device by means of a first and second control curve in a standby mode.

FIG. 1 shows an electrosurgical generator 100 with a control device 140 that is adapted to control a cooling device 120 by means of a first and second control curve CC1 and CC2 in a standby mode. A display device 190 may be connected to the control device 140.

The electrosurgical generator 100 is used for operating an electrosurgical instrument 200 that is connectable or connected to the generator 100. The generator 100 is configured for that purpose to supply the electrosurgical instrument 200 with a current and/or a voltage electrically, in particular with a high frequency current. The generator 100 is thus a HF generator. The generator 100 is connected with an electrical supply grid 300 and includes a power converter 170 for power supply of the instrument 200. The power con-verter 170 can also be referred to as switching device. The generated current provided to the instrument 200 can be higher, lower or inverted depending on the design of the power converter 170 and the requirements of the electrical load, respectively the electrosurgical instrument 200. The generator 100 may also include a rectifier 172 to convert the received AC current from the electrical supply grid 300. The generator 200 includes instrument terminals 160 or ports for connecting the electrosurgical instrument 200 with the generator for power supply and/or for data or signal exchange. An intermediate capacitor $C_{ZK}$ is arranged between the rectifier 172 and the power converter 170, which is used as a temporal energy buffer, in order to generate an HF output current at the instrument terminal 160.

The electrosurgical generator 100 comprises a housing 110. An active controllable cooling device 120 is used for removing heat energy generated within the housing 110, wherein the rotational speed of the cooling device 120 is temperature-controlled. At least one temperature sensor 130 is used for monitoring a temperature of a hardware component of the electrosurgical generator. The temperature sensor 130 is arranged in the area of the power converter 170. For example the temperature of the switching transistors of the power converter 170 are monitored. Those transistors are critical hardware components, which are monitored with the temperature sensors 130. One or more temperature sensors 130 may be used.

The electrosurgical generator 100 also comprises a control device 140 for controlling the cooling device 120. The cooling device 120 is for example a fan, which is indicated with a fan symbol. The cooling device 120 and the temperature sensors 130 are connected with the control device 140 with control or data lines. The control device 140 is adapted to control the cooling device 120 at least with a first control curve CC1 and a second control curve CC2.

Figure 3:
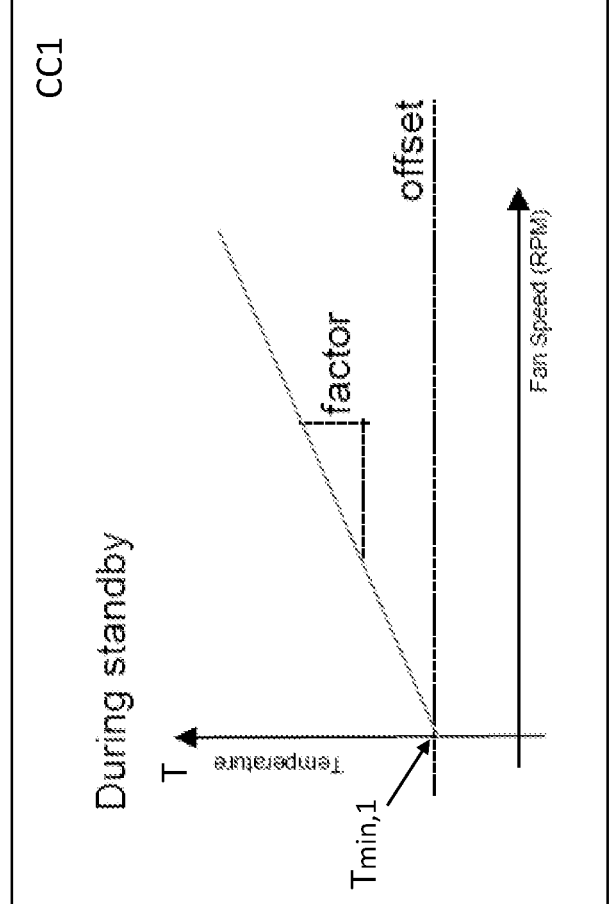
FIG. 3 shows a first control curve, which is used to control a cooling device during standby.

The first control curve CC1 is shown in FIG. 3 in more detail. The second control curve CC2 is shown in FIG. 4 in more detail.

The first control curve CC1 is used to control the rotational speed of the cooling device 120 depending on the monitored temperature T during a first operating mode of the electrosurgical generator 100, namely during the standby mode or the standby state. During standby no electrosurgical instrument 200 is connected to the electrosurgical generator 100 or a connected electrosurgical instrument 200 is not supplied with electrical power P from the electrosurgical generator 100, which is exemplary shown in FIG. 1 and indicated with "Standby".

The second curve CC2 is used to control the rotational speed of the cooling device 120 depending on the monitored temperature T during a second operating mode of the electrosurgical generator 100, namely during the activation mode or the activation state. During activation the electrosurgical instrument 200 is connected to the electrosurgical generator 100 and is supplied with electrical power P from the electrosurgical generator 100, which can be seen in FIG. 2 and which is indicated with the word "Activation".

Figure 4:
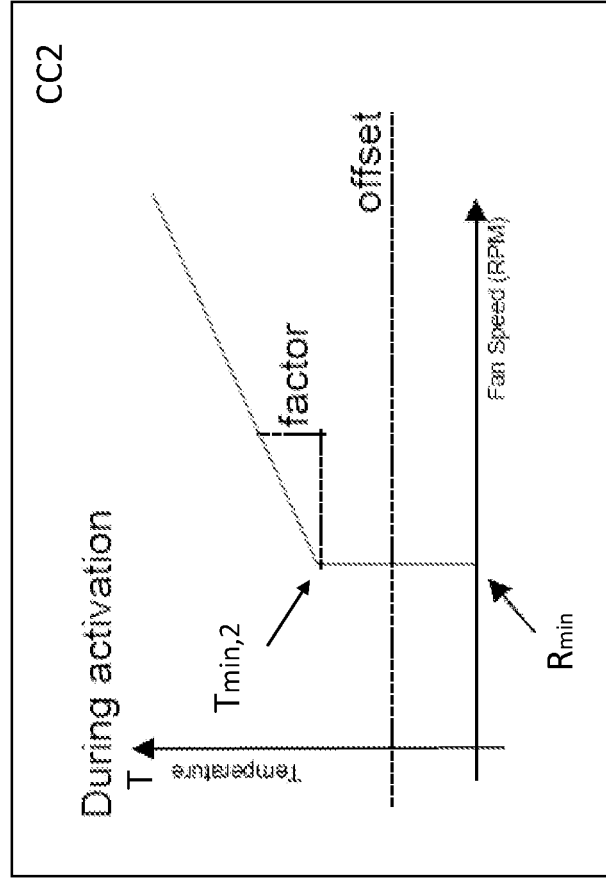
FIG. 4 shows second control curve, which is used to control a cooling device during activation.

The first control curve CC1 and the second control curve CC2 are different from each other, which can be seen, when comparing the course of both control curves, which can be seen in FIGS. 3 and 4 in more detail.

The electrosurgical generator 100 includes a manual trigger device 150, wherein the manual trigger device 150 is adapted to trigger a switching between the first operating mode and the second operating mode of the generator. The manual trigger device 150 is exemplary shown as an external foot switch connected to the electrosurgical generator 100 at an extra terminal of the generator 100. Triggering the foot switch triggers for example the HF mode or activation mode, as shown in FIG. 2.

The first control curve CC1 and the second control curve CC2 are part of the control device 140 and the switching between the two curves CC1 and CC2 is exemplified by a switch symbol 142. The switch only exemplifies that a switching between CC1 and CC2 is executed in the different operating states or modes of the generator. The switch device 142 is not necessarily a hardware switch. The switching device 142 may also be logic bit or a control signal or the like. The control curves CC1 and CC2 may be integrated in a nonvolatile memory or data store of the generator 100. The controls curves CC1 and CC2 might implemented in the control device 140 by means of a look-up tables or a data arrays or as a software algorithm or the like. During standby mode the control device 140 thus controls the cooling device 120 with a control signal CS which is depending on the course of the first control curve CC1.

Figure 2:
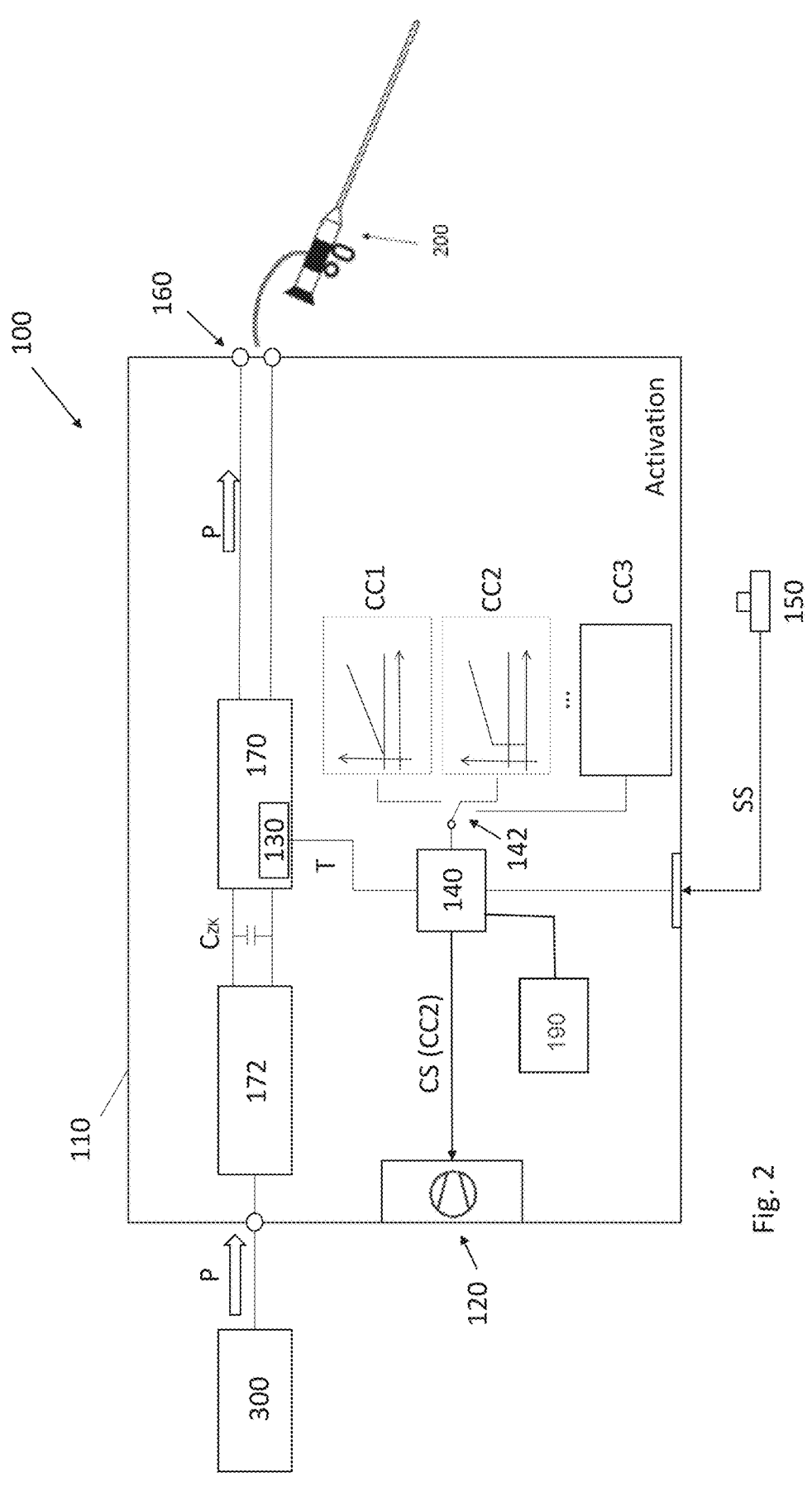
FIG. 2 shows the electrosurgical generator as shown in FIG. 1 in an activation mode.

FIG. 2 shows an electrosurgical generator 100 in an embodiment according to the invention with a control device 140 that is adapted to control a cooling device 120 by means of a first and second control curve CC1, CC2 in an activation mode. This mode is for example activated, when the manual trigger device 150 is triggered and a switchover signal SS is detected with the control device 140, which triggers the generator to change its operating mode from standby to activation mode, for instance. During activation mode the control device 140 controls the cooling device 120 with a control signal CS which is depending on the course of the second control curve CC2.

FIG. 3 shows a first control curve CC1, which is used to control a cooling device 120 during standby mode of the generator 100. As can be seen in FIG. 3 the first control curve CC1 increases the rotational speed RPM of the cooling device 120 depending on the monitored temperature T, in case the monitored temperature T of the hardware component exceeds a first minimum temperature value Tmin, 1. The rotational speed.

RPM of the cooling device 120 is set to zero, when the monitored temperature T is below the first minimum temperature value Tmin, 1. Above Tmin, 1 the first control curve CC1 increases the rotational speed RPM of the cooling device 120 with a rising function, when the measured temperature T increases. The rising function is linear rising function with a linear factor, which can be understood as slope.

FIG. 4 shows a second control curve CC2, which is used to control a cooling device 120 during activation mode of the generator 100. As can be seen in FIG. 4 the second control curve CC2 increases the rotational speed RPM of the cooling device 120 depending on the monitored temperature T, in case the monitored temperature T of the hardware component exceeds a second minimum temperature value Tmin,2. The rotational speed RPM of the cooling device 120 is set to minimum rotational speed value Rmin, when the monitored temperature T is below the second minimum temperature value Tmin,2. Above Tmin,2 the second control curve CC2 increases the rotational speed RPM of the cooling device 120 with a rising function, when the measured temperature T increases. The rising function is linear rising function with a linear factor, which can be understood as slope.

REFERENCE SIGN LIST

100 Electrosurgical generator
110 housing
120 cooling device
130 temperature sensor
140 control device
142 switching device
150 trigger device
160 instrument terminal
170 power converter
172 rectifier
200 electrosurgical instrument
300 electrical supply grid
CC1 first control curve
second control curve CC2
Tmin, 1 first minimum temperature value
Tmin,2 second minimum temperature value
Rmin minimum rotational speed value
SS switchover signal
CS control signal
T measured temperature
P electrical power
$C_{ZK}$ intermediate circuit capacitor

The invention claimed is:

1. An electrosurgical generator for operating an electrosurgical instrument, comprising:
   a housing;
   an active controllable cooling device for removing heat energy generated within the housing, wherein a rotational speed of the active controllable cooling device is temperature-controlled;
   at least one temperature sensor for monitoring a temperature of a hardware component of the electrosurgical generator; and
   a control device configured to control the active controllable cooling device, wherein:
      the control device is configured to control the active controllable cooling device at least with a first control curve and a second control curve;
      the first control curve is configured to control the rotational speed of the active controllable cooling device depending on a monitored temperature during a first operating mode of the electrosurgical generator;
      the second control curve is configured to control the rotational speed of the active controllable cooling device depending on the monitored temperature during a second operating mode of the electrosurgical generator; and
      the first control curve is different from the second control curve.

2. The electrosurgical generator according to claim 1, wherein:
   the first operating mode being a standby mode in which the electrosurgical instrument is not connected to the electrosurgical generator; or
   the electrosurgical instrument is connected to the electrosurgical generator and is not supplied with electrical power from the electrosurgical generator.

3. The electrosurgical generator according to claim 1, wherein:
   the second operating mode being an activation mode in which the electrosurgical instrument is connected to the electrosurgical generator and is supplied with electrical power from the electrosurgical generator.

4. The electrosurgical generator according to claim 1, comprising:
   a manual trigger device, wherein:
      the manual trigger device is adapted to trigger a switching between the first operating mode of the electrosurgical generator and the second operating mode of the electrosurgical generator.

5. The electrosurgical generator according to claim 4, wherein:
   the manual trigger device is one of a hand switch and a foot switch, the manual trigger device being connected to the electrosurgical generator; and
   the manual trigger device is one of a switching mean and an input mean, the manual trigger device being integrated into the housing of the electrosurgical generator.

6. The electrosurgical generator according to claim 1, wherein:
   the first control curve increases the rotational speed of the active controllable cooling device depending on the monitored temperature, in case the monitored temperature of the hardware component exceeds a first minimum temperature value; and
   the rotational speed of the active controllable cooling device is set to zero, when the monitored temperature is below the first minimum temperature value.

7. The electrosurgical generator according to claim 1, wherein:
   the second control curve increases the rotational speed of the active controllable cooling device depending on the monitored temperature, in case the monitored temperature of the hardware component exceeds a second minimum temperature value; and
   the rotational speed of the active controllable cooling device is set to minimum rotational speed value, when the monitored temperature is below the second minimum temperature value.

8. The electrosurgical generator according to claim 1, wherein:
   the control device is configured to control the active controllable cooling device additionally with a third control curve:
   the third control curve is configured to control the rotational speed of the active controllable cooling device depending on the monitored temperature; and
   the third control curve is activated, when the second operating mode is deactivated.

9. A method for operating an electrosurgical generator for operating an electrosurgical instrument, comprising:
   providing an active controllable cooling device for removing heat energy generated within a housing of the electrosurgical generator:
   monitoring a temperature of a hardware component of the electrosurgical generator by means of at least one temperature sensor; and
   controlling the active controllable cooling device by means of a control device, wherein:
      a controlling step includes controlling the active controllable cooling device with at least a first control curve and a second control curve:
      the first control curve is used to control a rotational speed of the active controllable cooling device depending on a monitored temperature during a first operating mode of the electrosurgical generator; and
      the second control curve is configured to control the rotational speed of the active controllable cooling device depending on the monitored temperature during a second operating mode of the electrosurgical generator.

10. The method according to claim 9, wherein:
   the first operating mode being a standby mode in which the electrosurgical instrument is not connected to the electrosurgical generator or a connected electrosurgical instrument is not supplied with electrical power from the electrosurgical generator; and/or
   the second operating mode is an activation mode in which the electrosurgical instrument is connected to the electrosurgical generator and is supplied with electrical power from the electrosurgical generator.

11. The method according to claim 9, further comprising:
   triggering a switching between the first operating mode of the electrosurgical generator and the second operating mode of the electrosurgical generator by means of a manual trigger device.

12. The method according to claim 9, wherein:
   a controlling step further comprising:
      increasing the rotational speed of the active controllable cooling device by means of the first control curve depending on the monitored temperature, in case the monitored temperature of the hardware component exceeds a first minimum temperature value; and

setting the rotational speed of the active controllable cooling device to zero, when the monitored temperature is below the first minimum temperature value.

13. The method according to claim 9, wherein:
a controlling step further comprises:
    increasing the rotational speed of the active controllable cooling device by means of the second control curve depending on the monitored temperature, in case the monitored temperature of the hardware component exceeds a second minimum temperature value; and
    setting the rotational speed of the active controllable cooling device to minimum rotational speed value, when the monitored temperature is below the second minimum temperature value.

14. An electrosurgical generator system comprising:
the electrosurgical generator configured according to claim 1; and
an electrosurgical instrument, wherein:
    the electrosurgical generator comprises at least one instrument terminal for connecting and electrically supplying power to the electrosurgical instrument:
    in operation of the electrosurgical generator system, the electrosurgical instrument is connected to the instrument terminal:
    the electrosurgical generator is adapted to perform a method for supplying power to the operate the electrosurgical instrument.

15. The electrosurgical generator according to claim 6, wherein:
    the first control curve increases the rotational speed of the active controllable cooling device with a rising function, when the monitored temperature increases, in particular with a linear rising function, a quadratic rising function or an exponential rising function; and
    the rising function is a manual adjustable function, which can be displayed at a display device of the electrosurgical generator and can be adjusted by user inputs.

16. The electrosurgical generator according to claim 7, wherein:
    the second control curve increases the rotational speed of the active controllable cooling device with a rising function, when the monitored temperature increases, in particular with a linear rising function, a quadratic rising function or an exponential rising function; and
    the rising function is a manual adjustable function, which can be displayed at a display device of the electrosurgical generator and can be adjusted by user inputs.

17. The electrosurgical generator according to claim 8, wherein:
    the third control curve is different from the first control curve and the second control curve:
    the rotational speed of the active controllable cooling device is set to a cool down rotational speed value by means of the third control curve; and the third control curve is activated until a predefined time duration is reached or until a predefined temperature of the hardware component is reached.

18. The method according to claim 12, wherein:
the controlling step comprises:
    increasing the rotational speed of the active controllable cooling device with the first control curve by means of a rising function, when the monitored temperature increases, in particular increasing the rotational speed by means of a linear rising function, a quadratic rising function or an exponential rising function; and
    providing a manual adjustable function as rising function, which can be displayed at a display device of the electrosurgical generator and can be adjusted by user inputs.

19. The method according to claim 13, wherein:
the controlling step comprises:
    increasing the rotational speed of the active controllable cooling device with the second control curve by means of a rising function, when the monitored temperature increases, in particular increasing the rotational speed by means of a linear rising function, a quadratic rising function or an exponential rising function; and
providing a manual adjustable function as rising function, which can be displayed at a display device of the electrosurgical generator and can be adjusted by user inputs.

20. A method of operating the electrosurgical generator for supplying power to the electrosurgical instrument according to claim 14, comprising:
    providing the active controllable cooling device for removing the heat energy generated within the housing of the electrosurgical generator;
    monitoring the temperature of the hardware component of the electrosurgical generator by means of the at least one temperature sensor; and
    controlling the active controllable cooling device by means of the control device, including:
    controlling the active controllable cooling device with at least the first control curve and the second control curve, wherein:
    the first control curve is configured to control the rotational speed of the active controllable cooling device based on the monitored temperature during the first operating mode of the electrosurgical generator, and
    the second control curve is configured to control the rotational speed of the active controllable cooling device based on the monitored temperature during the second operating mode of the electrosurgical generator.

* * * * *